(12) United States Patent
Xiao et al.

(10) Patent No.: US 10,398,375 B2
(45) Date of Patent: Sep. 3, 2019

(54) WEARABLE DEVICE AND PHYSIOLOGICAL INFORMATION MONITORING SYSTEM AND METHOD

(71) Applicant: HTC Corporation, Taoyuan (TW)

(72) Inventors: Bo-Wen Xiao, Taoyuan (TW);
Ming-Tien Lin, Taoyuan (TW);
Tun-Chun Yang, Taoyuan (TW);
Chih-Jen Hu, Taoyuan (TW)

(73) Assignee: HTC Corporation, Taoyuan (TW)

( * ) Notice: Subject to any disclaimer, the term of this patent is extended or adjusted under 35 U.S.C. 154(b) by 296 days.

(21) Appl. No.: 14/972,100

(22) Filed: Dec. 17, 2015

(65) Prior Publication Data
US 2017/0172500 A1 Jun. 22, 2017

(51) Int. Cl.
*A61B 5/00* (2006.01)
*A61B 5/0205* (2006.01)

(52) U.S. Cl.
CPC .......... *A61B 5/6803* (2013.01); *A61B 5/0006* (2013.01); *A61B 5/0015* (2013.01); *A61B 5/0205* (2013.01); *A61B 5/681* (2013.01); *A61B 5/742* (2013.01)

(58) Field of Classification Search
CPC ... A61B 5/6803; A61B 5/0006; A61B 5/0015; A61B 5/0205; A61B 5/681; A61B 5/742
See application file for complete search history.

(56) References Cited

U.S. PATENT DOCUMENTS

| | | | |
|---|---|---|---|
| 9,603,524 B2 * | 3/2017 | Park | A61B 5/0002 |
| 2008/0243393 A1* | 10/2008 | Yamamoto | A61B 5/02416 |
| | | | 702/19 |
| 2015/0119654 A1* | 4/2015 | Martin | A61B 5/0059 |
| | | | 600/301 |

FOREIGN PATENT DOCUMENTS

| | | |
|---|---|---|
| CN | 104287703 | 1/2015 |
| TW | M486395 | 9/2014 |
| TW | 201538125 | 10/2015 |

OTHER PUBLICATIONS

"Office Action of Taiwan Counterpart Application", dated Feb. 22, 2017, p. 1-p. 7, in which the listed references were cited.
Office Action of China Counterpart Application, dated Sep. 28, 2018, pp. 1-9.

* cited by examiner

*Primary Examiner* — Paula J Stice
(74) *Attorney, Agent, or Firm* — JCIPRNET

(57) ABSTRACT

The invention provides a wearable device, a physiological information monitoring system and a physiological information monitoring method. The wearable device includes a device body, a measurement circuit, and a measurement trigger interface. The measurement circuit is disposed on the device body and adapted to perform a physiological information measurement operation to measure a physiological signal and generate physiological information accordingly. The measurement trigger interface is triggered to generate a measurement trigger signal. The measurement circuit performs the physiological information measurement operation in response to the measurement trigger signal.

14 Claims, 14 Drawing Sheets

WEARABLE DEVICE AND PHYSIOLOGICAL INFORMATION MONITORING SYSTEM AND METHOD

BACKGROUND OF THE INVENTION

1. Field of the Invention

The invention relates to a physiological information monitoring technology, and particularly relates to a wearable device, a physiological information monitoring system, and a physiological information monitoring method.

2. Description of Related Art

With the development in health technologies, there have been many wearable devices focusing on health care on the market. Such devices usually include a plurality of kinds of measurement circuits adapted to capture the user's physiological signals when the user wears the device and transmit data collected by using an application to a cloud server for further integration and analyses or display the data on a screen as reference of medical consideration, so that the user may be informed of his/her health status immediately.

Since it usually requires a long time to collect and calculate data in connection with physiological info illation, so as to more accurately reflect the user's physiological status, the measurement circuit in the conventional wearable device used for health care is usually designed to perform a physiological information measurement operation at a pre-determined time interval, so as to cope with the needs of operating for a long period of time and avoid excessive power consumption of the wearable device.

However, in the measurement of the conventional wearable device, since the measurement interval of the measurement circuit is set in advance, the user is unable to determine the time point of measuring the physiological signal. Thus, if the user suddenly feel uncomfortable, the measurement circuit of the conventional wearable device is unable to measure the physiological information immediately.

SUMMARY OF THE INVENTION

The invention provides a wearable device, a physiological information monitoring system, and a physiological information monitoring method that touch upon the issues at hands.

A wearable device according to an embodiment of the invention includes a device body, a measurement circuit, and a measurement trigger interface. The measurement circuit is disposed on the device body and adapted to perform a physiological information measurement operation to measure a physiological signal and generate physiological information accordingly. The measurement trigger interface is triggered to generate a measurement trigger signal. The measurement circuit performs the physiological information measurement operation in response to the measurement trigger signal.

A physiological information monitoring system according to an embodiment of the invention includes a wearable device and a monitoring terminal device. The wearable device includes a device body and a measurement circuit. One of the wearable device and the monitoring terminal device includes a measurement trigger interface. The measurement circuit is disposed on the device body and adapted to perform a physiological information measurement operation to measure a physiological signal and generate physiological information accordingly. The monitoring terminal device is adapted to receive and display the physiological information. The measurement trigger interface is triggered to generate a measurement trigger signal. The measurement circuit performs the physiological information measurement operation in response to the measurement trigger signal.

A physiological information monitoring method according to an embodiment of the invention includes steps as follows: providing a measurement trigger interface; performing a physiological information measurement operation to measure a physiological signal when the measurement trigger interface is triggered; and generating physiological information based on the measured physiological signal.

Based on above, the invention provides the wearable device, the physiological information monitoring system, and the physiological information monitoring method that provide the measurement trigger interface for the user to trigger. The user may make the measurement circuit in the wearable device measure the current physiological signal of the user in real time and generate the corresponding physiological information by triggering the measurement trigger interface at any time. Compared with the conventional wearable device capable of monitoring physiological information, the wearable device of the embodiments of the invention allows the user to directly control the measurement operation in a more intuitive way.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
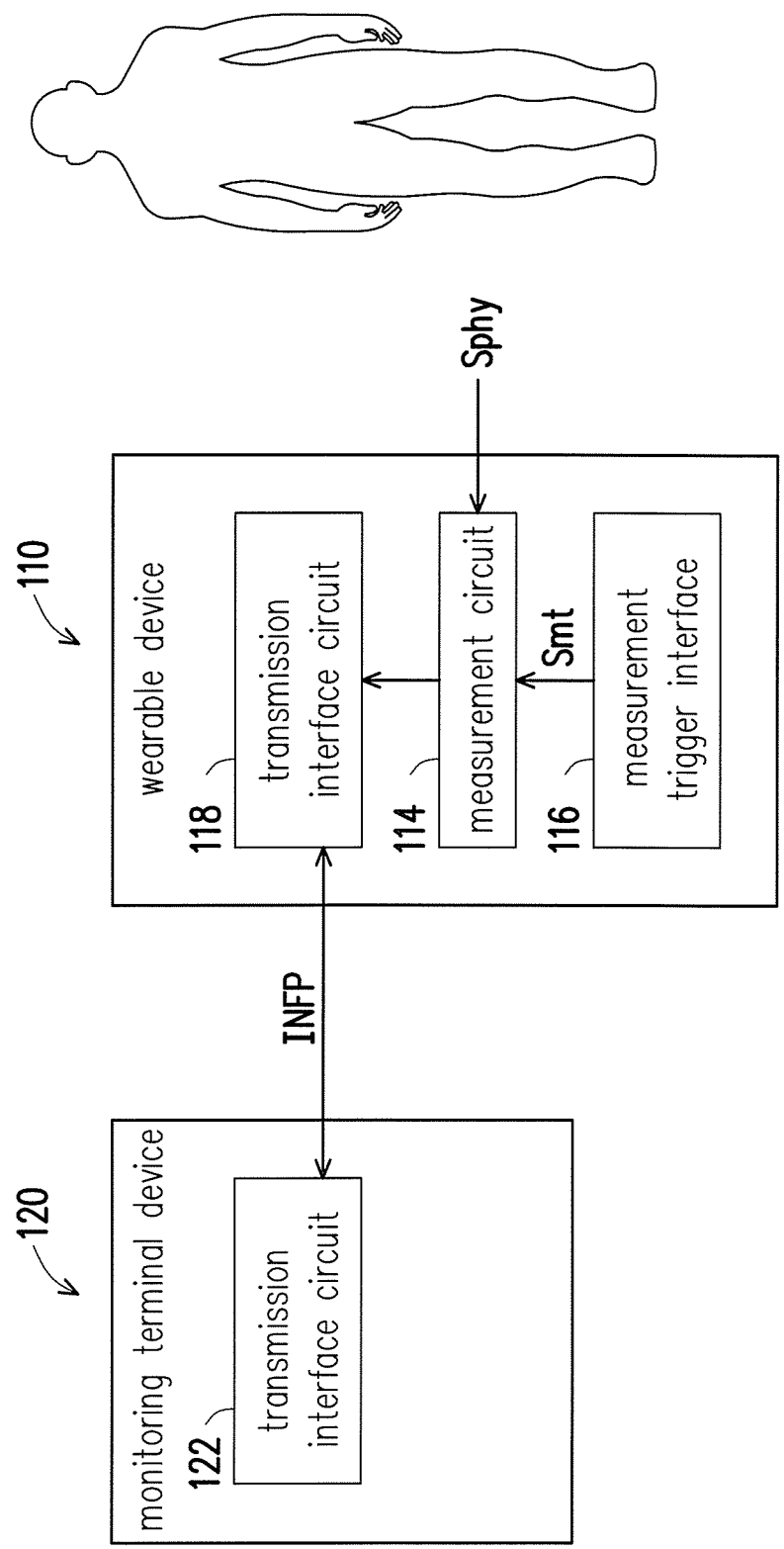
FIG. 1 is a schematic block view illustrating functions of a physiological monitoring system according to an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

In order to make the disclosure more comprehensible, embodiments are described below as the examples to practice the disclosure accordingly. Moreover, elements/components/steps with same reference numerals represent same or similar parts in the drawings and embodiments.

FIG. 1 is a schematic block view illustrating functions of a physiological monitoring system according to an embodiment of the invention. Referring to FIG. 1, a physiological information monitoring system 100 of this embodiment may be adapted to monitor/record the user's physiological information. The physiological information may be, for example, physiological data of the human body that may serve as reference for diagnosis, such as body temperature, heart rate, perspiration, electrocardiography (ECG), photoplethysmography (PPG), heart rate variability, blood pressure, pulse wave velocity, respiratory rate, or skin conductance (SC). In this embodiment, the physiological information monitoring system 100 includes a wearable device 110 and a monitoring terminal device 120.

The wearable device 110 may be any device in a form that the user may wear. For example, the wearable device 110 may be a wristband device, a chest strap device, or a head mounted device, etc. Relevant embodiments will be specifically described in the subsequent paragraphs. However, the invention does not intend to impose any limitation in this regard.

In this embodiment, the wearable device 110 includes a device body 112, a measurement circuit 114, a measurement trigger interface 116, and a transmission interface circuit 118. The device body 112 may be adapted to accommodate circuit elements and have a structural design allowing the user to wear. For example, if the wearable device 110 is a chest strap device, the wearable device 112 may be designed as a chest strap structure for the user to tie and fix the wearable device 110 at the chest. If the wearable device 110 is a wristband device, the device body 112 may be designed as a watch structure for the user to wear the wearable device 110 on the user's wrist. If the wearable device 110 is a head mounted device, the device body 112 may be designed as a headset structure or a headband structure for the user to fix the wearable device 110 at a head position (e.g., a position near the ear or the forehead, but the invention is not limited thereto). In other words, the structure of the device body of this embodiment may be designed in correspondence with the type of the wearable device 110, and the invention does not intend to impose a limitation in this regard.

The measurement circuit 114 is disposed on the device body 112 and adapted to perform a physiological information measurement operation to measure a physiological signal Sphy of the user that wears the wearable device 110 and generate physiological information INFP accordingly. In addition, the physiological information INFP may be transmitted to the monitoring terminal device 120 in a wired or wireless manner, such that the user may retrieve the measured physiological information INFP from the monitoring terminal device 120.

In this embodiment, the specific hardware arrangement of the measurement circuit 114 may be determined based on the type of the physiological signal Sphy to be measured. For example, if the physiological signal Sphy to be measured is an ECG signal or a skin conductance signal, the measurement circuit 114 may be arranged as an electronic signal measurement circuit having a plurality of electrodes and a signal processing circuit. If the physiological signal Sphy to be measured is a PPG signal, the measurement signal may be arranged as an optical measurement circuit including a light emitting element, a light sensing element, and a signal processing circuit. In other words, even though the circuit structure and arrangement of the measurement circuit 114 are not described in detail in this embodiment, people having ordinary skills in the art should understand that the measurement circuit 114 may be implemented in various possible circuit configurations based on the needs for measuring different physiological signals after referring to the descriptions herein.

The measurement trigger interface 116 of this embodiment is disposed on the device body 112 and provides an interface for the user to trigger. When the user triggers the measurement trigger interface 116, the measurement trigger interface 116 may generate a measurement trigger signal Smt and transmit the measurement trigger signal Smt that is generated to the measurement circuit 114, such that the measurement circuit 114 performs the physiological information measurement operation in response to the measurement trigger signal Smt.

In this embodiment, the measurement trigger interface 116 may be implemented as a physical button or a virtual button. For example, in an example of implementing the measurement trigger interface 116 as a physical button, the measurement trigger interface 116 may be a mechanical switch or a thin-film switch, for example. In an example of implementing the measurement trigger interface 116 as a virtual button, the measurement trigger interface 116 may be a touch switch (such as a capacitive, resistive, or optical touch switch, but the invention does not intend to impose a limitation in this regard), for example.

The transmission interface circuit 118 is disposed on the device body 112 and coupled to the measurement circuit 114, and serves to provide a wired transmission interface (e.g., universal serial bus (USB), mini-USB, etc., but the invention does not intend to impose a limitation in this regard) or a wireless transmission interface (e.g., Wi-Fi, bluetooth, etc., but the invention does not intend to impose a limitation in this regard). In addition, the wearable device 110 and the monitoring terminal device 120 may transmit signals to each other through the wired or wireless transmission interface.

It should also be noted that the wearable device 110 of this embodiment is not limited to only including the above circuits. Corresponding circuit elements may be disposed based on functional requirements. For example, when implemented as a wristband device, the wearable device 110 may further include a timing circuit and a display module, etc., so as to display time information. The invention does not intend to impose a limitation on an additional function provided by the wearable device 110.

The monitoring terminal device 120 may be any type of electronic device, such as a server, a desktop computer, a laptop computer, a tablet computer, a smartphone, etc. The monitoring terminal device 120 includes a transmission interface circuit 122. In addition, the transmission interface circuit 122 and the transmission interface circuit 118 of the wearable device 110 have the same/corresponding transmission interface. Therefore, the monitoring terminal device 120 may receive the physiological information INFP measured by the wearable device 110 in a wired or wireless manner and display the physiological information INFP.

In an embodiment of wired transmission, the transmission interface circuit 118 and the transmission interface 122 may be corresponding connection ports (not shown), for example. In the wearable device 110 and the monitoring terminal device 120, the connection ports may be connected with physical circuits, such that signals may be transmitted between the wearable device 110 and the monitoring terminal device 120 through the physical circuits and the connection ports.

In an embodiment of wireless transmission, the transmission interface circuit 118 and the transmission interface circuit 122 may be wireless transmission modules (not shown) compatible with the same wireless transmission interface. In addition, signals may be transmitted between the wearable device 110 and the monitoring terminal device 120 through the wireless transmission interface.

Several embodiments of configurations of the wearable device 110 in different forms are described in the following with reference to FIGS. 2A to 2D.

Figure 2A:
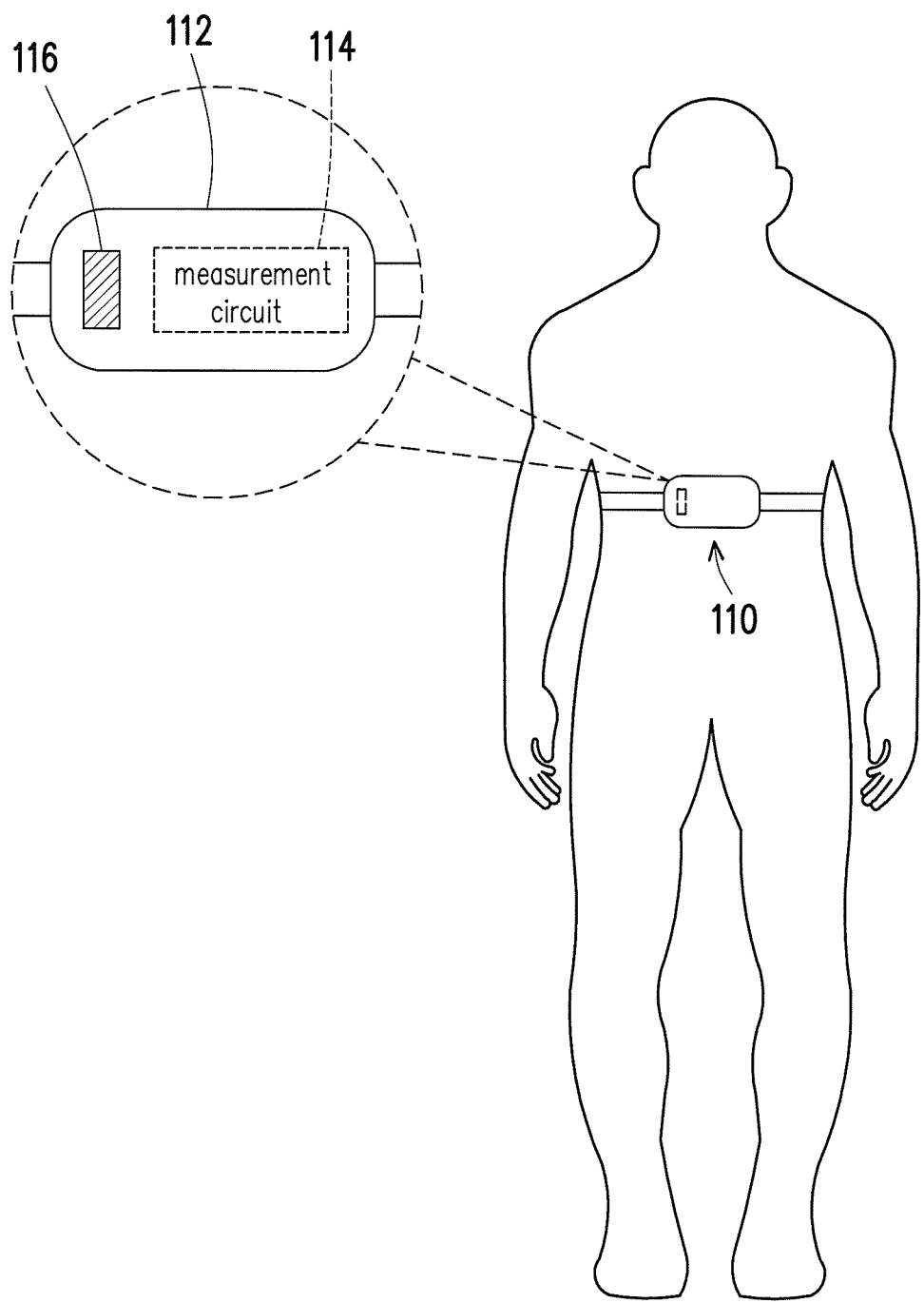
FIG. 2A is a schematic view illustrating an arrangement and use of a wearable device according to an embodiment of FIG. 1.

Referring to FIG. 2A, the wearable device 110 of this embodiment is described as a chest strap device, for example. In this embodiment, the device body 112 is designed as a chest strap structure, for example, and may be worn at or near the chest. The measurement circuit 114 may be disposed on the device body 112, and a measurement part is disposed at a side contacting the user's body, so as to measure the physiological signal Sphy of the user. If the measurement circuit is an electronic signal measurement circuit, the measurement part may be an electrode, for example, and if the measurement circuit is an optical signal measurement circuit, the measurement part may be a light emitting element or a light sensing element, for example. The measurement trigger interface 116 of this embodiment is implemented on the device body 112 as a physical button (referred to as a measurement button 116 herein). The user may make the measurement circuit 114 perform the physiological information measurement operation by pressing the measurement button 116. However, the invention is not limited thereto.

Figure 2B:
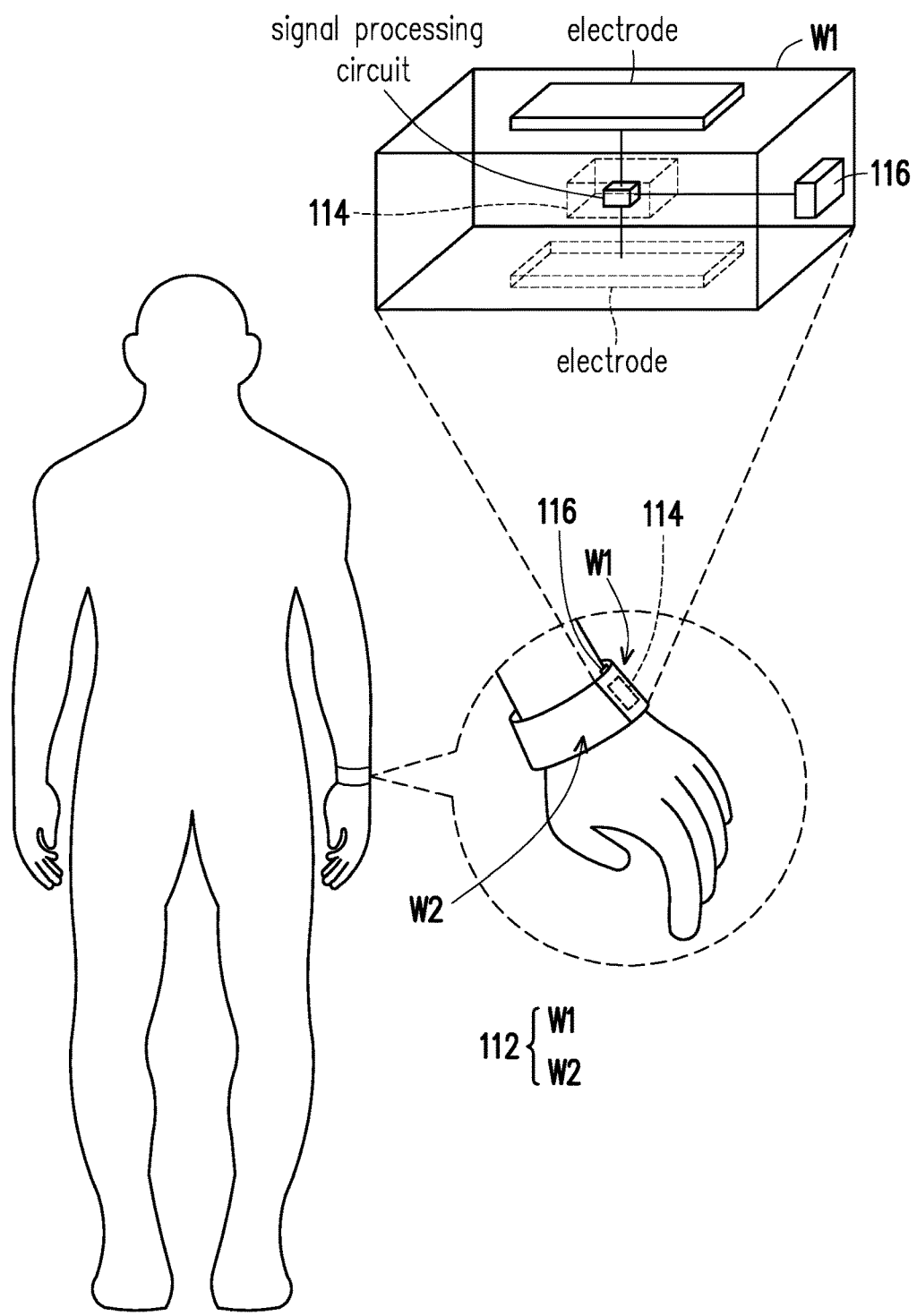
FIG. 2B is a schematic view illustrating an arrangement and use of a wearable device according to another embodiment of FIG. 1.

Referring to FIG. 2B, the wearable device 110 of this embodiment is described as a wristband device, for example. In this embodiment, the device body 112 is designed as a watch structure having a watch body W1 and a watch band W2, and may be worn on the user's wrist. The measurement circuit 114 may be disposed on the watch body W1 and the measurement part thereof is disposed at a side contacting the user's body, so as to measure the physiological signal Sphy of the user. The measurement trigger interface 116 of this embodiment is shown as a physical button (referred to as the measurement button 116 herein) disposed at the side edge of the watch body, for example. The user may make the measurement circuit 114 perform the physiological information measurement operation by pressing the measurement button 116. However, the invention is not limited thereto.

It should also be noted that, in the application of the wristband device, an additional electrode needs to be disposed at the chest or on the watch body if the ECG signal is to be measured. The user may contact the additional electrode with the hand without the wristband device to establish a conductive circuit to measure the ECG signal.

Figure 2C:
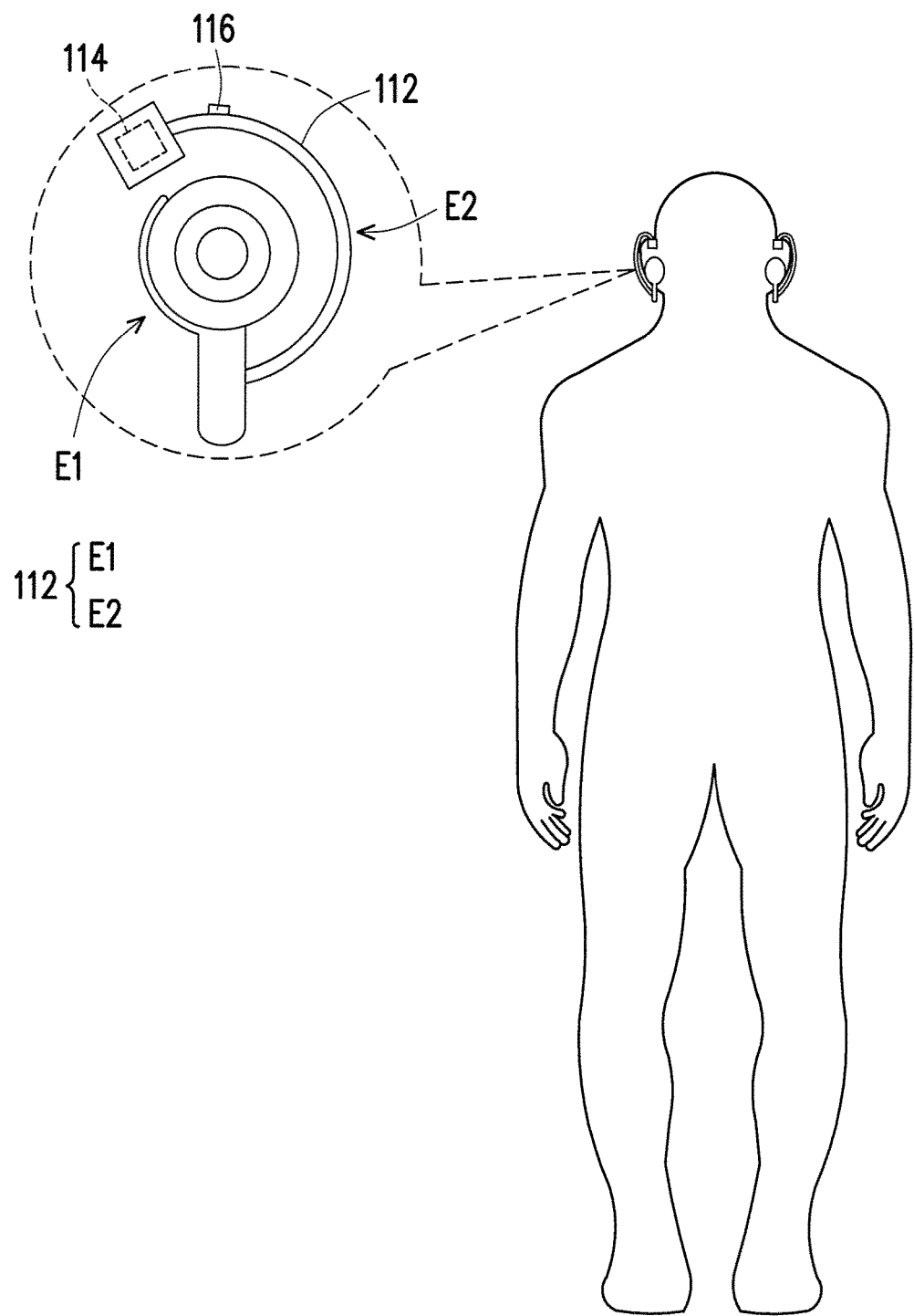
FIG. 2C is a schematic view illustrating an arrangement and use of a wearable device according to yet another embodiment of FIG. 1.

Referring to FIG. 2C, the wearable device 110 of this embodiment is a head mounted device, for example. In this embodiment, the device body 112 is an ear set structure including an ear plug part E1 and a fixing part E2, for example, and may be worn on the user's ear. The measurement circuit 114 may be disposed on the fixing part E2 and the measurement part thereof is disposed at a side contacting the user's body, so as to measure the physiological signal Sphy of the user. The measurement trigger interface 116 of this embodiment is shown as a physical button (referred to as the measurement button 116 herein) disposed on the fixing part E2, for example. The user may make the measurement circuit 114 perform the physiological information measurement operation by pressing the measurement button 116. However, the invention is not limited thereto.

Figure 2D:
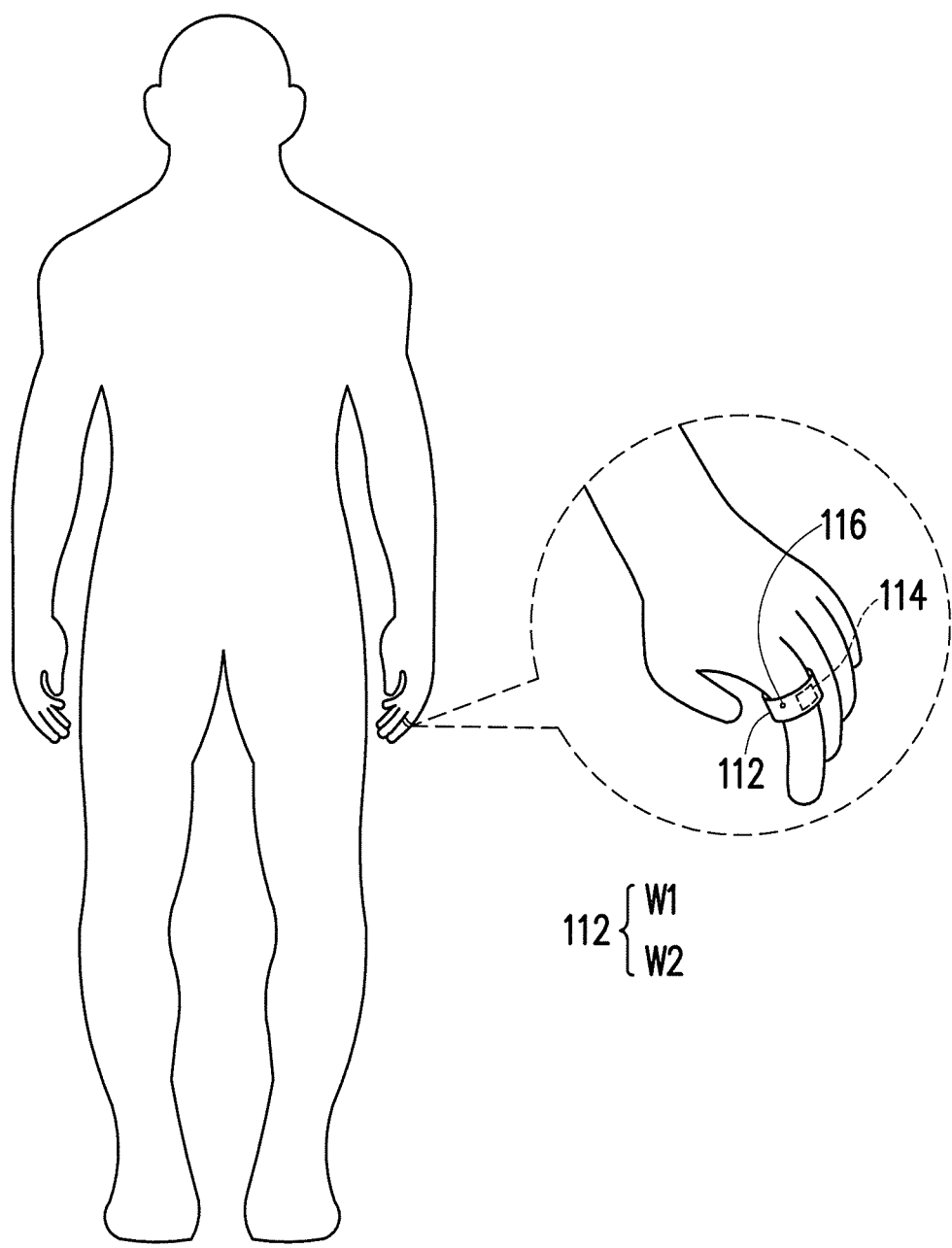
FIG. 2D is a schematic view illustrating an arrangement and use of a wearable device according to still another embodiment of FIG. 1.

Referring to FIG. 2D, the wearable device 110 of this embodiment is described as a ring device, for example. In this embodiment, the device body 112 is an annular body structure designed as a ring, for example, and may be worn on the user's finger. The measurement circuit 114 may be disposed in the annular body structure and the measurement part is disposed at a side contacting the user's body, so as to measure the physiological signal Sphy of the user. The measurement trigger interface 116 of this embodiment is shown as a physical button (referred to as the measurement button 116 herein) disposed on the annular body structure, for example. The user may make the measurement circuit 114 perform the physiological information measurement operation by pressing the measurement button 116. However, the invention is not limited thereto.

Based on the configurations of the wearable device 110, the user may trigger the measurement trigger interface 116 to make the measurement circuit 114 measure the current physiological signal Sphy in real time at any time and generate the corresponding physiological infatuation INFP. Compared with the conventional wearable device capable of monitoring physiological information, the physiological information monitoring system 100 and the wearable device 110 of the embodiment provides a measurement operation that is more intuitive and allows the user to control directly. Besides, since the user may immediately measure the current physiological status when feeling uncomfortable, the physiological information monitoring system 100 of this embodiment is able to provide more representative physiological information for subsequent interpretation of medical data, such that the cause of the user's discomfort may be diagnosed more easily.

Figure 3:
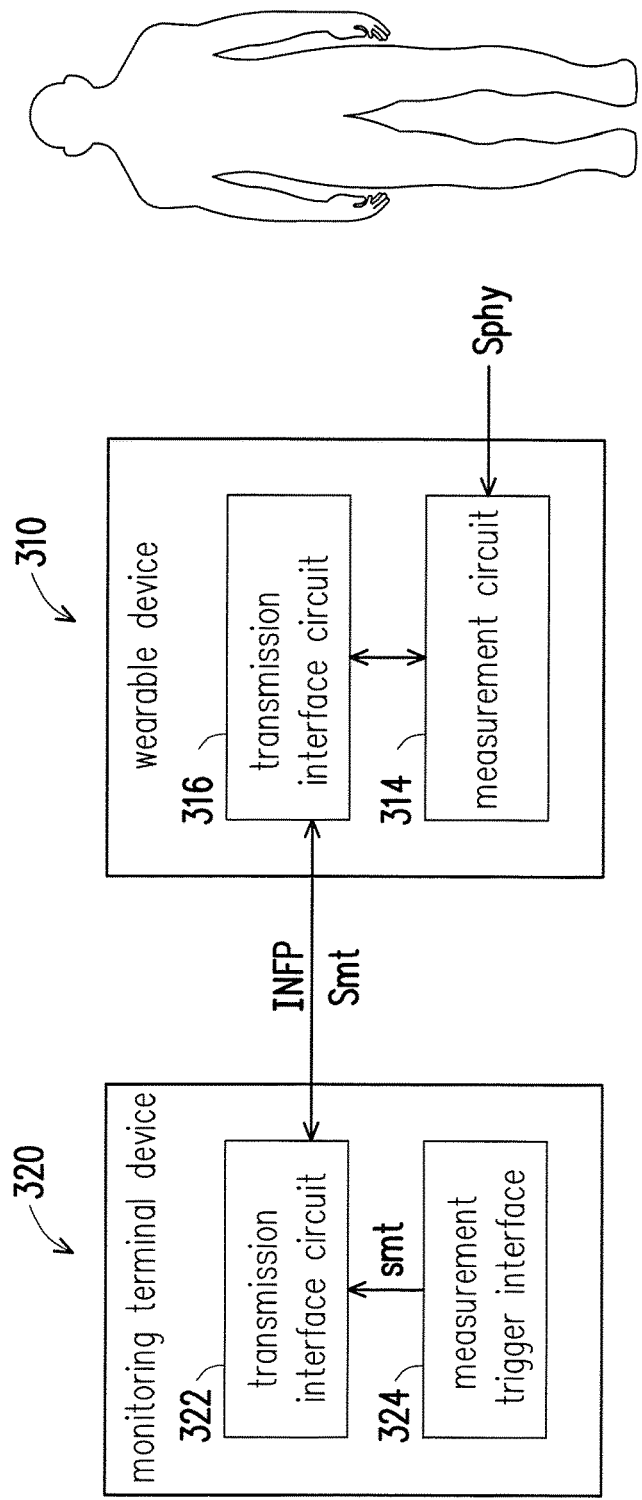
FIG. 3 is a schematic block view illustrating functions of a physiological monitoring system according to another embodiment of the invention.

FIG. 3 is a schematic block view illustrating functions of a physiological monitoring system according to another embodiment of the invention. Referring to FIG. 3, a physiological information monitoring system 300 of this embodiment includes a wearable device 310 and a monitoring terminal device 320. In addition, the wearable device 310 includes a device body 312, a measurement circuit 314, and a transmission interface circuit 316. Also, the monitoring terminal device 320 includes a transmission interface circuit 322 and a measurement trigger interface 324.

The physiological information monitoring system 300 of this embodiment is substantially similar with the physiological information monitoring system 100. A main difference therebetween is that the measurement trigger interface 322 of this embodiment is disposed in the monitoring terminal device 320, instead of being disposed in the wearable device 310.

More specifically, in this embodiment, when the measurement trigger interface 324 is triggered by the user, the measurement trigger signal Smt may be transmitted to the wearable device 310 through the transmission interface circuit 322. From the perspective of the wearable device 310, the wearable device 310 may receive the measurement trigger signal Smt through the transmission interface circuit 316 and provide the transmission trigger signal Smt to the measurement circuit 314, such that the measurement circuit 314 performs the physiological signal measurement operation when receiving the measurement trigger signal Smt.

Figure 4:
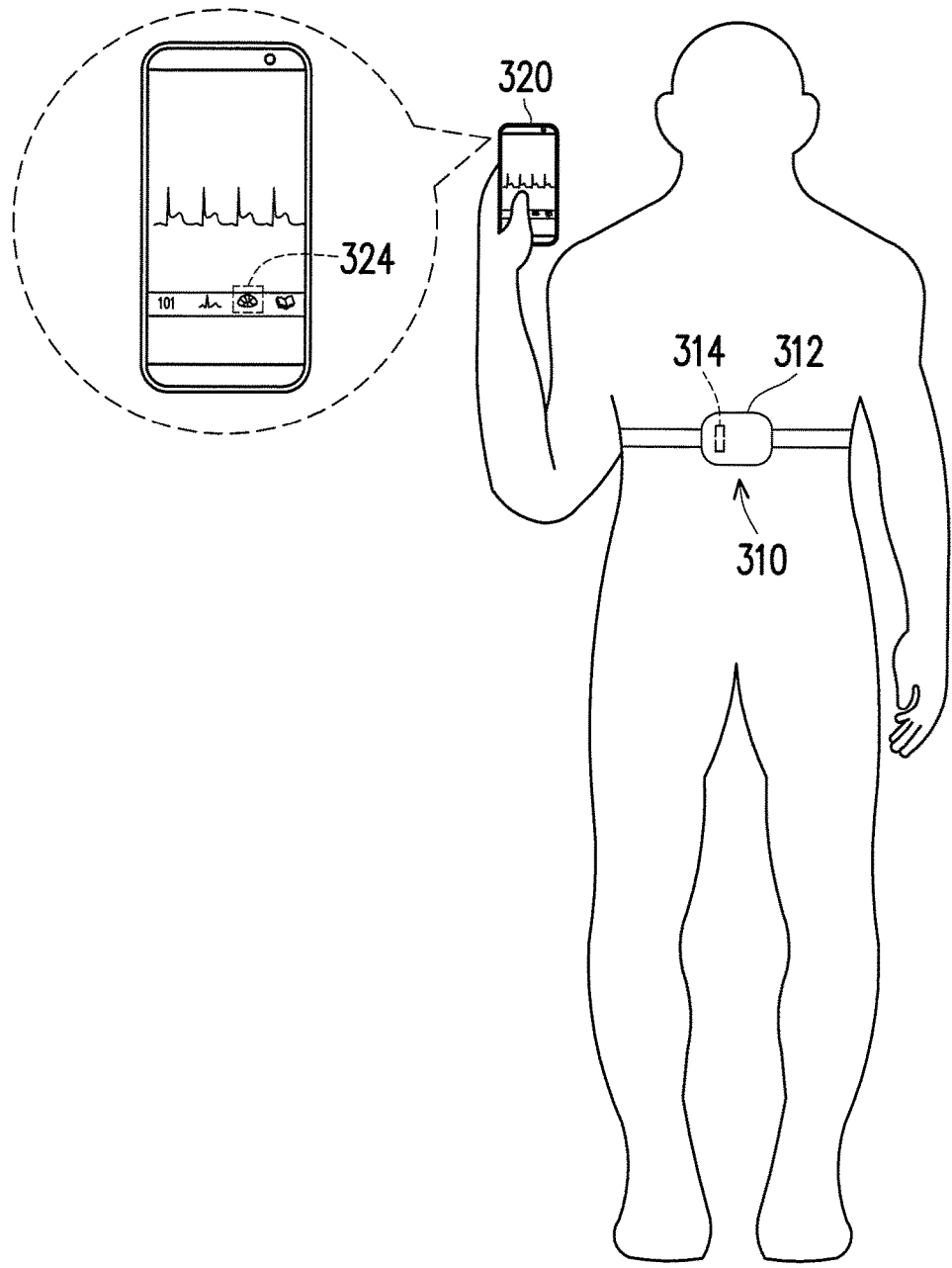
FIG. 4 is a schematic view illustrating an arrangement and use of a wearable device according to an embodiment of FIG. 3.

FIG. 4 is a schematic view illustrating an arrangement and use of a wearable device according to an embodiment of FIG. 3. The wearable device 310 of this embodiment is described as a chest strip device, for example. However, the wearable device 310 may also be designed as a wristband device or a head mounted device with reference to FIGS. 2B and 2C, and the invention does not intend to impose a limitation in this regard. Also, the monitoring terminal device 320 of this embodiment is shown as a smartphone, for example. However, the invention does not intend to impose a limitation in this regard, either.

Referring to FIG. 4, in this embodiment, the measurement trigger interface 324 is shown as a virtual button (referred to as a measurement button 324 herein). The user may trigger the smartphone to transmit the measurement trigger signal Smt to the wearable device 310 through the wireless transmission circuit 322 by clicking the measurement button 324 on the smartphone. The wearable device 310 may receive the measurement trigger signal Smt through the wireless transmission circuit 316 and provide the measurement trigger signal Smt to the measurement circuit 314, such that the measurement circuit 314 performs the physiological information measurement operation in response to the measurement trigger signal Smt.

Figure 5:
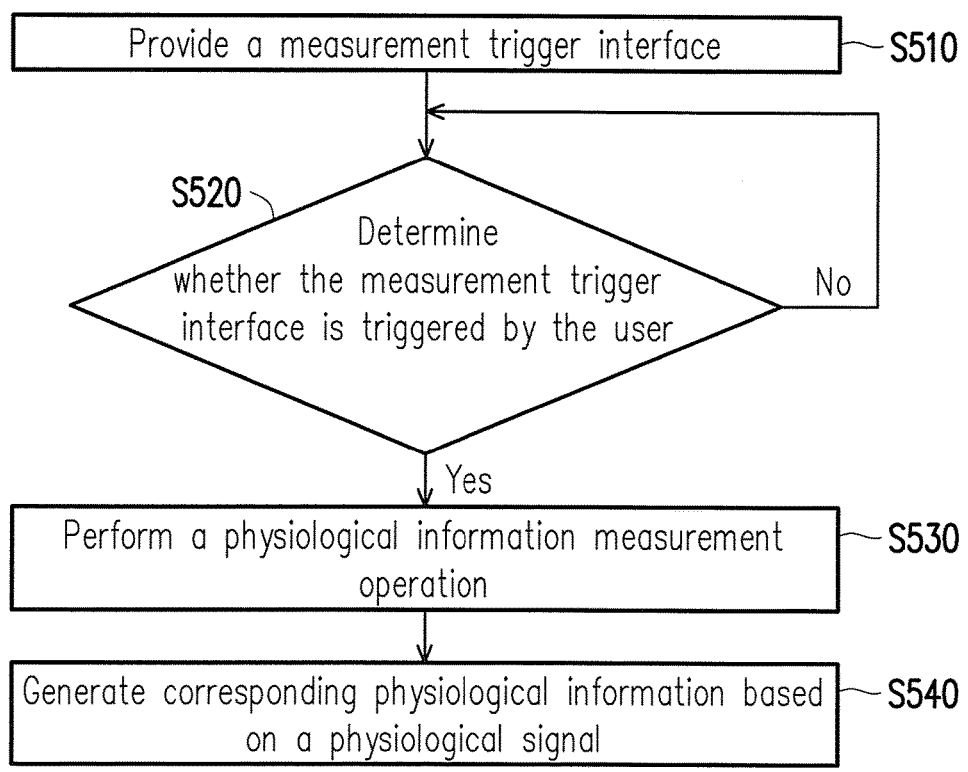
FIG. 5 is a flowchart view illustrating a physiological information monitoring method according to an embodiment of the invention.

FIG. 5 is a flowchart view illustrating a physiological information monitoring method according to an embodiment of the invention. The physiological information monitoring method of this embodiment may be used in the frameworks of the physiological information measurement system shown in FIGS. 1 to 4. Referring to FIG. 5, in the physiological information monitoring method of this embodiment, the measurement trigger interface for the user to trigger is provided in the wearable device or the monitoring terminal device (Step S510), and whether the measurement trigger interface is triggered by the user is determined continuously (Step S520).

If it is determined that the user triggers the measurement trigger interface, the wearable device may perform the physiological information measurement operation, so as to measure the physiological signal of the user (Step S530). Then, the wearable device generates the corresponding physiological information based on the measured physiological signal (Step S540).

Figure 6A:
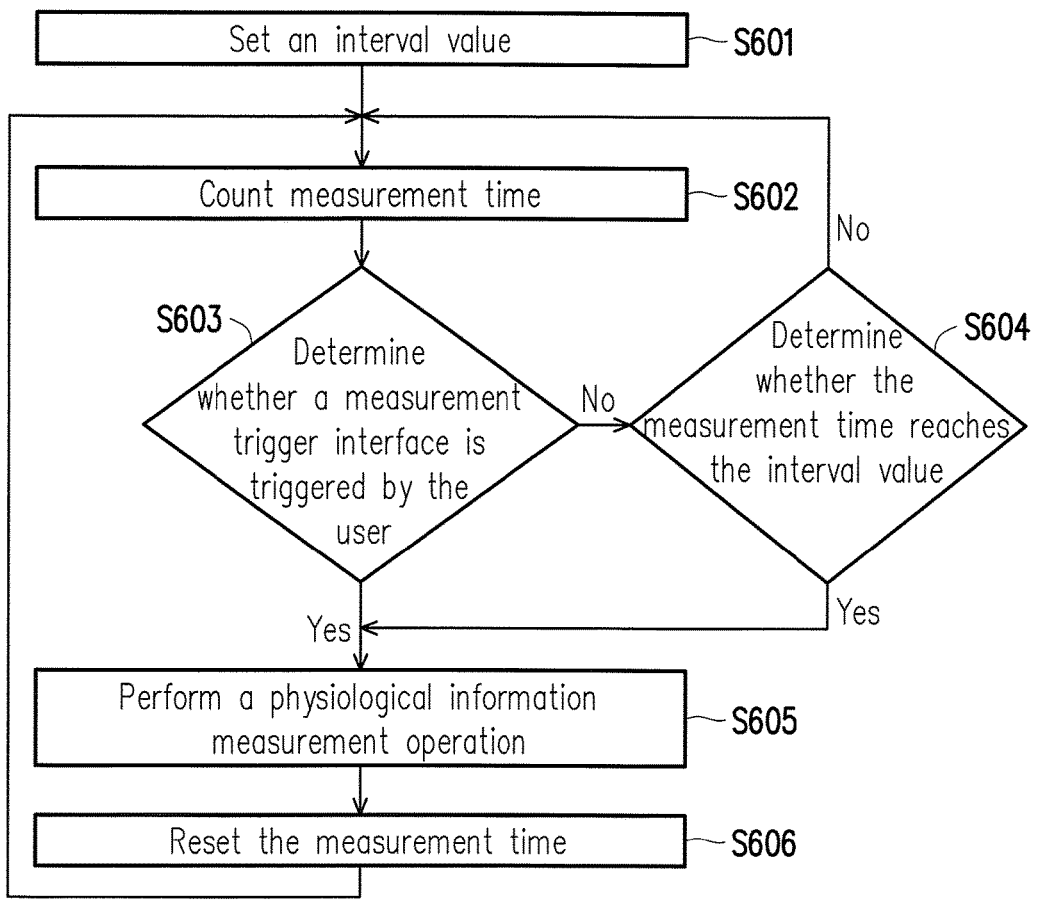
FIG. 6A is a flowchart view illustrating a physiological information monitoring method according to a first embodiment of FIG. 5.
Figure 7A:
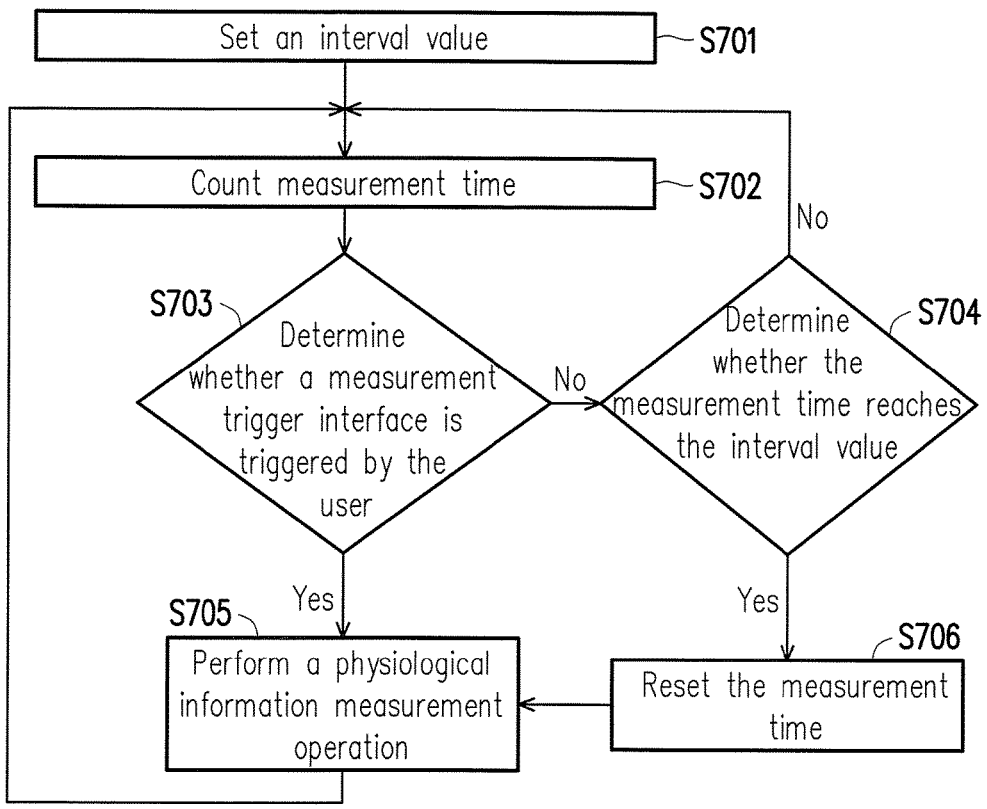
FIG. 7A is a flowchart view illustrating a physiological information monitoring method according to a second embodiment of FIG. 5.
Figure 7B:
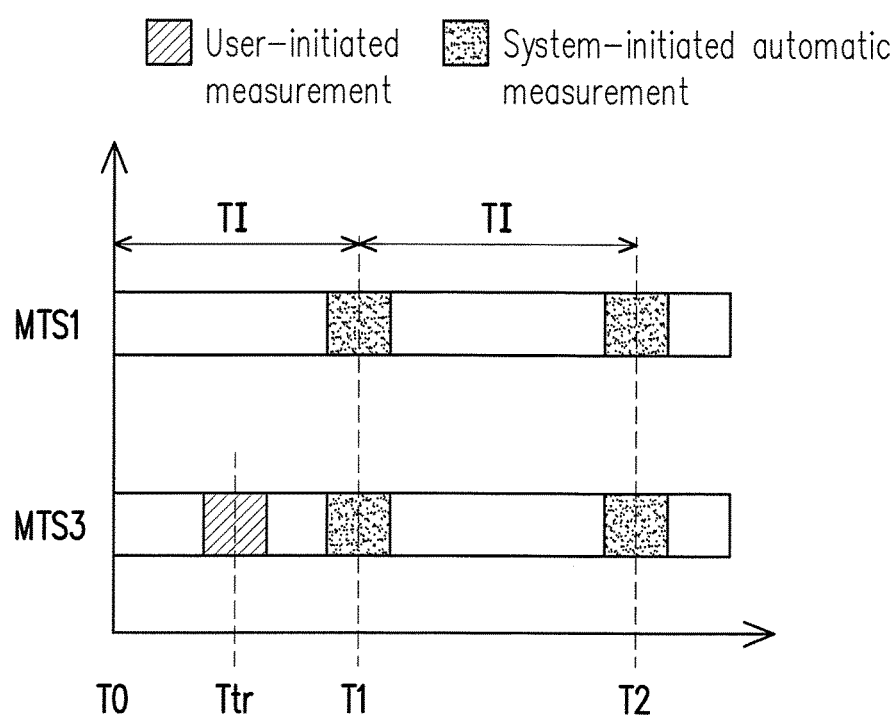
FIG. 7B is a schematic view illustrating a measurement sequence of the physiological information monitoring method of the second embodiment.
Figure 8A:
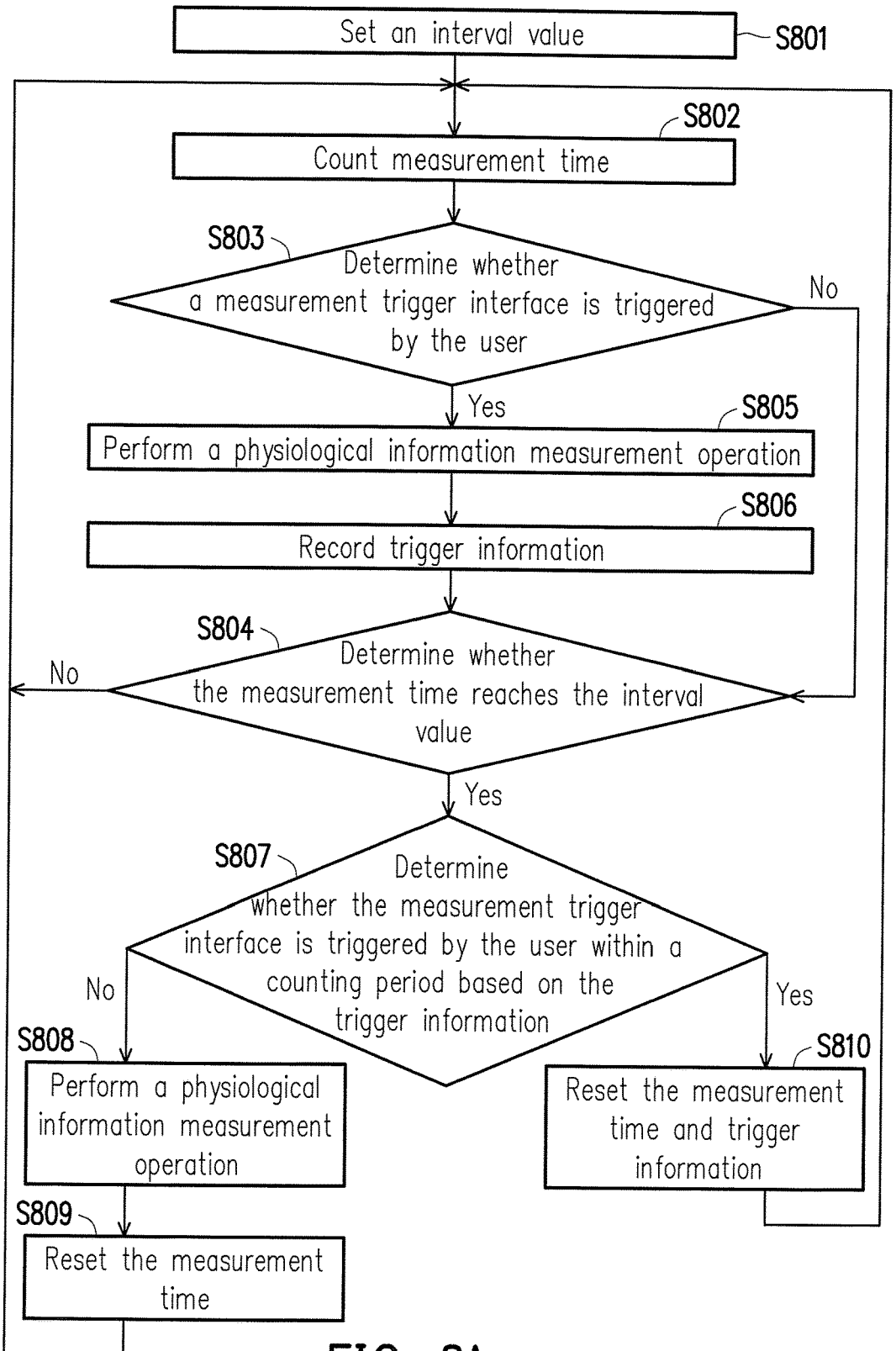
FIG. 8A is a flowchart view illustrating a physiological information monitoring method according to a third embodiment of FIG. 5.
Figure 8B:
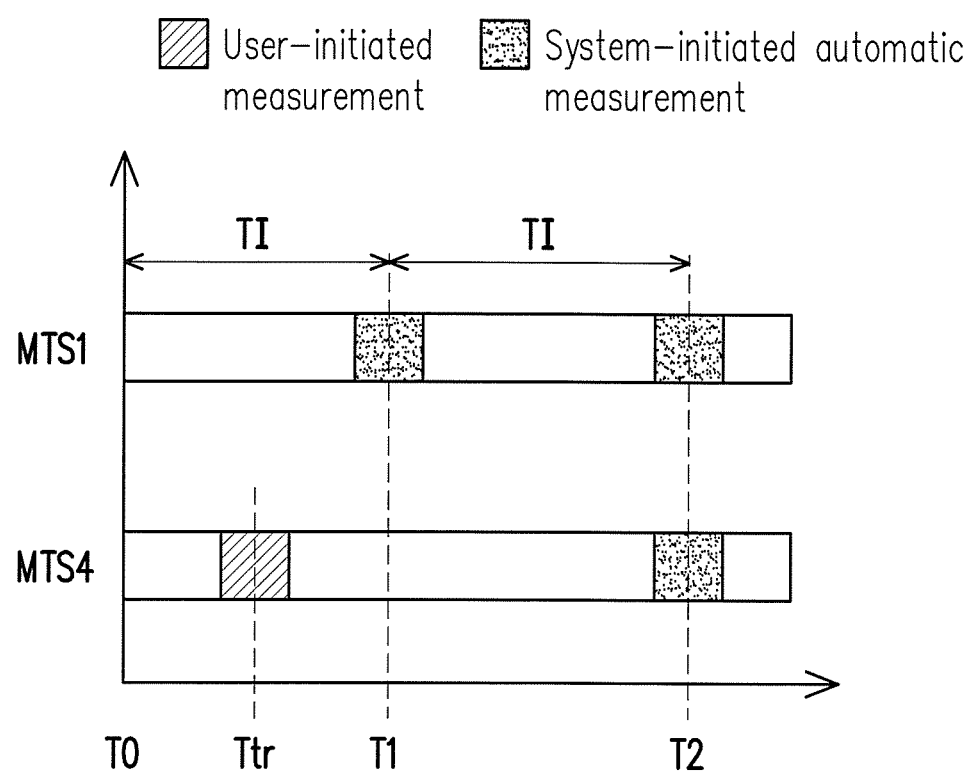
FIG. 8B is a schematic view illustrating a measurement sequence of the physiological information monitoring method of the third embodiment.

In addition to controlling the wearable device to perform the physiological information measurement operation based on the user's active triggering, the embodiment is further integrated with the conventional process of automatic measurement performed at a predetermined time interval, so as to make an overall measurement process of the wearable device more desirable. In the following, the embodiments in FIG. 6A to FIG. 8B are provided to describe the steps and sequences of the steps of the physiological information monitoring method where the measurement triggered by the user and the automatic measurement of the system are used together. Here, FIGS. 6A and 6B illustrate a flowchart and a measurement sequence of the physiological information monitoring method of the first embodiment, FIGS. 7A and 7B illustrate a flowchart and a measurement sequence of the physiological information monitoring method of the second embodiment, and FIGS. 8A and 8B illustrate a flowchart and a measurement sequence of the physiological information monitoring method of the third embodiment.

Figure 6B:
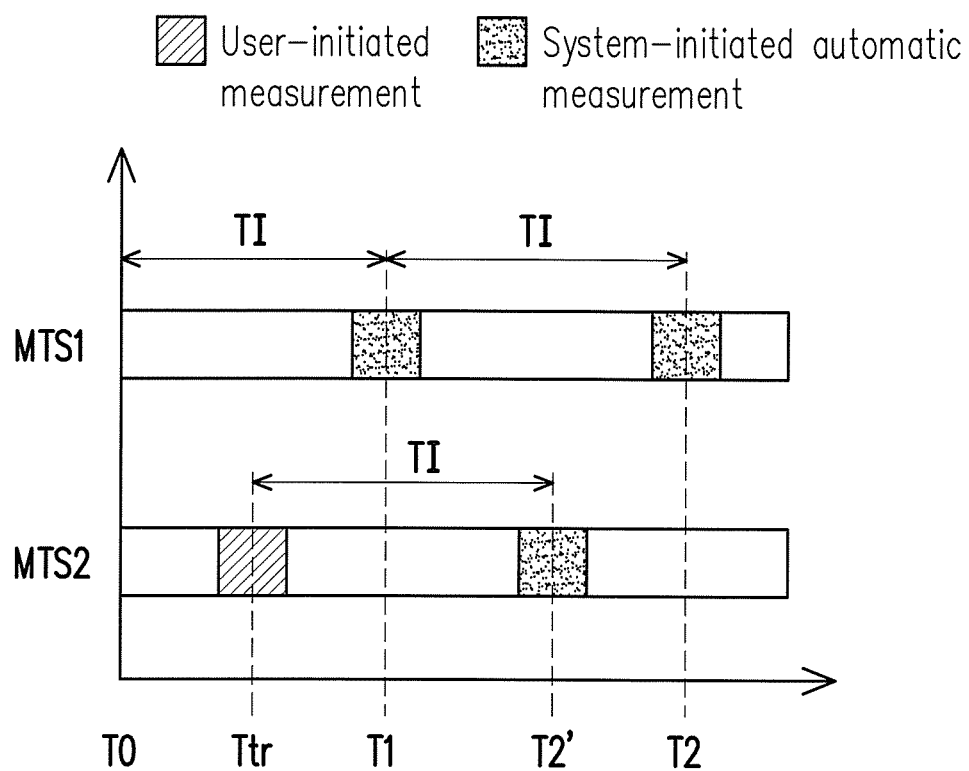
FIG. 6B is a schematic view illustrating a measurement sequence of the physiological information monitoring method of the first embodiment.

Referring to FIGS. 6A and 6B together, in this embodiment, the user may set an interval value TI based on needs before turning on the wearable device for measurement (Step S610). The interval value TI may serve as reference of time interval for the system to perform automatic measurement.

After the wearable device is turned on, the wearable device may start counting measurement time (Step S602) and determine whether the measurement trigger interface is triggered by the user (Step S603), and whether the measurement time reaches the interval value TI (Step S604).

Under the circumstance that the measurement trigger interface is not triggered by the user (No in Step S603), as shown in a measurement sequence MTS1, when the measurement time is within time T0 to time T1, since the wearable device determines that the measurement time does not reach the interval value TI (No in Step S604), the process returns to Step S602 of counting the measurement time. When the measurement time reaches the time T1, the wearable device determines that the measurement time reaches the interval value TI (Yes in Step S604), and the physiological information measurement operation is performed (Step S605). After the wearable device performs the physiological information measurement operation at the time T1, the measurement time that is counted is reset (Step S606), and the process returns to Step S602 to count the time again.

Similarly, under the circumstance that the measurement trigger interface is not triggered by the user, the wearable device may automatically perform the physiological information measurement operation again when the measurement time reaches time T2.

Under the circumstance that the measurement trigger interface is triggered by the user at time Ttr (Yes in Step S603), as shown in a measurement sequence MTS2, the wearable device may perform the physiological information measurement operation at the time Ttr in response to the user's triggering of the measurement trigger interface (Step S605), and the measurement time that is counted is reset after the time Ttr (Step S606), and the process returns to Step S602 to count the time again.

More specifically, in this embodiment, since the measurement time is also reset due to the user's triggering of the measurement operation, the initial time point that the wearable device starts counting time again in the measurement sequence MTS2 is the time Ttr. Therefore, the wearable device does not perform the physiological information measurement operation again at the time T1, but perform the physiological information measurement operation again at time T2' (i.e., Ttr+TI) after the interval value TI has passed since the time Ttr.

Referring to FIGS. 7A and 7B, Steps S701 to S706 of this embodiment are substantially similar to Steps S601 to S606 in the previous embodiment. A main difference therebetween is that, in this embodiment, after the wearable device determines that the user triggers the measurement trigger interface (Yes in Step S703) and performs the physiological information measurement operation (Step S705), the process returns to Step S702 of counting the measurement time without resetting the measurement time that is counted. The measurement time is only reset when the wearable device determines that the accumulated measurement time reaches the interval value Ti.

As shown in a measurement sequence MTS3 in FIG. 7B, even if the wearable device performs the physiological information measurement operation at the time Ttr in response to the user's triggering, the wearable device still performs the physiological information measurement operation at the time T1 because the measurement time is not reset. In other words, in this embodiment, regardless of whether the user triggers the measurement trigger interface or not, the wearable device automatically performs the physiological information measurement operation at every predetermined time interval (interval value TI) from the time T0.

Referring to FIGS. 8A and 8B, Steps S801 to S805 of this embodiment are substantially similar to Steps S601 to S605 and Steps S701 to S705 in the previous embodiments. The embodiment mainly differs from the previous embodiments in that, when the wearable device determines that the user triggers the measurement trigger interface, the wearable device may record trigger information that the measurement trigger interface is triggered (Step S806) and determine whether to automatically perform the physiological information measurement operation when the accumulated measurement time reaches the interval value TI based on whether the measurement trigger interface is triggered during a counting period according to the trigger information.

More specifically, as shown the measurement sequence MTS1, if the wearable device determines that the measurement trigger interface is not triggered within the counting period, the wearable device may perform the physiological information measurement operation and reset the measurement time when the measurement time reaches the interval value TI (Step S809).

On the contrary, as shown in the measurement sequence MTS4, if the wearable device determines that the measurement trigger interface is triggered at the time Ttr, the wearable device may record the trigger information indicating that the user triggers the measurement trigger interface after the time Ttr, determines that the user initiates the physical information measurement operation within the counting period based on the trigger information when the measurement time reaches the interval value TI, and reset the measurement time and the trigger information accordingly without performing the physiological information measurement operation.

In other words, in this embodiment, the wearable device determines whether the user triggers the measurement trigger interface in each counting period (e.g., the period from the time T0 to the time T1, the period from the time T1 to the time T2). If the wearable device determines that the user triggers the measurement trigger interface within the counting period, the physiological information measurement operation originally scheduled to be automatically performed by the system is canceled. On the contrary, if the wearable device determines that the user does not trigger the measurement trigger interface within the counting period, the physiological information measurement operation is performed at the specific time T1 and T2 based on the predetermined interval value TI.

It should be noted that the steps in the first to third embodiments are merely provided to describe the concept, and the specific steps to carry out the method are not limited to those shown in the drawings. For example, the determining step in each process (i.e., the step of determining whether the measurement trigger interface is triggered, the step of determining whether the measurement time reaches the interval value, and the step of determining whether the measurement trigger interface is triggered within the counting period) may be performed in sequence or simultaneously, and the invention does not intend to impose a limitation in this regard. In other words, a wearable device falls within the scope of the first to third embodiments of the invention as long as the physiological information monitoring method with the measurement sequences MTS1 to MTS4 as shown in FIGS. 6B, 7B, and 8B is adopted.

In view of the foregoing, the invention provides the wearable device, the physiological information monitoring system, and the physiological information monitoring method that provide the measurement trigger interface for the user to trigger. The user may make the measurement circuit in the wearable device measure the current physiological signal of the user in real time and generate the corresponding physiological information by triggering the measurement trigger interface at any time. Compared with the conventional wearable device capable of monitoring physiological information, the wearable device of the embodiments of the invention provides a measurement operation that is more intuitive and allows the user to control directly. Besides, since the user may immediately measure the current physiological status when feeling uncomfortable, the physiological information monitoring system of this embodiment is able to provide more representative physiological information for subsequent interpretation of medical data, such that the cause of the user's discomfort may be diagnosed more easily.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:
1. A wearable device configured to be worn as a wristband device, comprising:
 a watch band; and
 a watch body physically connecting to the watch band and comprising:
  a measurement circuit disposed within the watch body and comprising:
   two electrocardiography (ECG) electrodes extending from the watch body to detect an ECG signal; and
   a signal processing circuit disposed within the watch body and electrically connecting to the ECG electrodes and configured to detect, through the ECG electrodes, a physiological signal to generate physiological information accordingly; and
  a measurement trigger interface disposed within the watch body through which a user generates a measurement trigger signal which triggers the measurement circuit to measure the physiological information, wherein the measurement circuit is configured to measure a first physiological information in response to the measurement time reaching a first predetermined interval value, measure a second physiological information in response to receiving the measurement trigger signal, skip measuring a third physiological information in response to receiving the measurement trigger signal as the measurement time reaching a second predetermined interval value, and measure a fourth physiological information in response to the measurement time reaching the third predetermined interval value, wherein the first, second, and third predetermined interval value have the same duration.

2. The wearable device as claimed in claim 1, wherein the measurement circuit resets the measurement time and trigger information when the counted measurement time reaches the first predetermined interval value.

3. The wearable device as claimed in claim 1, wherein the measurement circuit resets the measurement time when receiving the measurement trigger signal.

4. The wearable device as claimed in claim 1, wherein the measurement trigger interface is disposed on the device body as a physical button or a virtual button.

5. The wearable device as claimed in claim 1, further comprising:
   a transmission interface circuit, disposed on the watch device body, coupled to the measurement circuit, and adapted to provide a wired transmission interface or a wireless transmission interface.

6. The wearable device as claimed in claim 5, wherein the transmission interface circuit receives the measurement trigger signal through the wired transmission interface or the wireless transmission interface and triggers the measurement circuit to measure the physiological information, or the transmission interface circuit sends the physiological information measured by the measurement circuit through the wired transmission interface or the wireless transmission interface.

7. A physiological information monitoring system, comprising:
   a wearable device configured to be worn as a wristband device, comprising:
      a watch band; and
      a watch body physically connecting to the watch band and comprising:
         a measurement circuit disposed within the watch body and comprising:
         two electrocardiography (ECG) electrodes extending from the watch body to detect an ECG signal; and
         a signal processing circuit disposed within the watch body and electrically connecting to the ECG electrodes and configured to detect, through the ECG electrodes, a physiological signal to generate physiological information accordingly; and
      a monitoring terminal device, adapted to display the physiological information which is received through a measurement trigger interface disposed within the monitoring terminal device, wherein a user generates a measurement trigger signal through the measurement trigger interface which triggers the measurement circuit to measure the physiological information, wherein the measurement circuit is configured to measure a first physiological information in response to the measurement time reaching a first predetermined interval value, measure a second physiological information in response to receiving the measurement trigger signal, skip measuring a third physiological information in response to receiving the measurement trigger signal as the measurement time reaching a second predetermined interval value, and measure a fourth physiological information in response to the measurement time reaching the third predetermined interval value, wherein the first, second, and third predetermined interval value have the same duration.

8. The physiological information monitoring system as claimed in claim 7, wherein the wearable device further comprises:
   a transmission interface circuit, disposed on the watch device body, coupled to the measurement circuit, and adapted to provide a wired transmission interface or a wireless transmission interface, wherein the wearable device receives the measurement trigger signal or sends the physiological information through the wired transmission interface or the wireless transmission interface.

9. The physiological information monitoring system as claimed in claim 7, wherein the measurement trigger interface is disposed on the monitoring terminal device as a physical button or a virtual button.

10. The physiological information monitoring system as claimed in claim 7, wherein the measurement circuit resets the measurement time and trigger information when the counted measurement time reaches the first predetermined interval value.

11. The physiological information monitoring system as claimed in claim 7, wherein the measurement circuit resets the measurement time when receiving the measurement trigger signal.

12. A physiological information monitoring method used by a wearable device configured to be worn as a wristband device, the method comprising:
   providing a watch band;
   providing a watch body physically connecting to the watch band and comprising:
      a measurement circuit disposed within the watch body and comprising:
         two electrocardiography (ECG) electrodes extending from the watch body to detect an ECG signal; and
         a signal processing circuit disposed within the watch body and electrically connecting to the ECG electrodes and configured to detect, through the ECG electrodes, a physiological signal to generate physiological information accordingly;
   providing a measurement trigger interface through which a user generates a measurement trigger signal, which triggers the measurement circuit to measure physiological information;
   generating physiological information based on the measured physiological signal; and
   wherein the measurement circuit measures a first physiological information in response to the measurement time reaching a first predetermined interval value, measure a second physiological information in response to receiving the measurement trigger signal, skip measuring a third physiological information in response to receiving the measurement trigger signal as the measurement time reaching a second predetermined interval value, and measures a fourth physiological information in response to the measurement time reaching the third predetermined interval value, wherein the first, second, and third predetermined interval value have the same duration.

13. The physiological information monitoring method as claimed in claim 12, further comprising:
   resetting the measurement time and trigger information when the measurement time reaches the first predetermined interval value.

14. The physiological information monitoring method as claimed in claim 12, further comprising:

resetting the measurement time when the measurement trigger interface is triggered.

* * * * *